United States Patent [19]

Alexander et al.

[11] Patent Number: 5,527,947
[45] Date of Patent: Jun. 18, 1996

[54] PROCESS FOR PREPARATION OF CINNAMATE SUNSCREEN AGENTS

[75] Inventors: Anatoly Alexander, Berkeley Heights; Ratan K. Chaudhuri, Butler, both of N.J.

[73] Assignee: ISP Van Dyk Inc., Belleville, N.J.

[21] Appl. No.: 358,438

[22] Filed: Dec. 19, 1994

[51] Int. Cl.$^6$ ........................................... C07C 69/76
[52] U.S. Cl. ........................................... 560/55; 562/465
[58] Field of Search ........................... 560/55; 562/465

[56] References Cited

FOREIGN PATENT DOCUMENTS 0044976  3/1982  European Pat. Off. .

*Primary Examiner*—Paul J. Killos
*Attorney, Agent, or Firm*—Marilyn J. Maue; Joshua J. Ward

[57] ABSTRACT

This invention relates to an improved process for the manufacture of cinnamate compounds, particularly sunscreen agents, useful in cosmetic skin and hair care formulations. The process comprises: (a) dissolving a water insoluble $C_1$ to $C_4$ alkoxy benzaldehyde and a $C_1$ to $C_4$ alkyl acetate in a common hydrocarbon solvent; (b) reacting the resulting solution in the presence of a strong alkali metal-containing base under mild conditions to form a mixture containing the corresponding $C_1$ to $C_4$ alkyl $C_1$ to $C_4$ alkoxy cinnamate, the alkali metal salt of the enol corresponding to the $C_1$ to $C_4$ alkyl $C_1$ to $C_4$ alkoxy cinnamate, the alkali metal salt of a $C_1$ to $C_4$ alkoxycinnamic acid, and a $C_1$ to $C_4$ alkanol; (c) acidifying the resulting mixture with from about 0.5 to about 1 mole of a strong polybasic acid per mole of base to release acetic acid, to convert the alkali metal salt of the $C_1$ to $C_4$ alkoxycinnamic acid to the corresponding $C_1$ to $C_4$ alkoxycinnamic acid and to form an alcohol suspension of an alkali metal salt of said strong polybasic acid; (d) esterifying said acetic acid with a $C_1$ to $C_4$ alkanol and stripping the resulting acetic acid ester from the mixture; (e) reacting the remaining $C_1$ to $C_4$ alkyl $C_1$ to $C_4$ alkoxycinnamate and $C_1$ to $C_4$ alkoxycinnamic acid with a $C_5$ to $C_{14}$ alkanol in the presence of said strong polybasic acid alkali metal salt suspension at a temperature of from about 60° to about 130° C.; and (f) recovering the $C_5$ to $C_{14}$ alkyl $C_1$ to $C_4$ alkoxy cinnamate as a product of the process.

20 Claims, No Drawings

PROCESS FOR PREPARATION OF CINNAMATE SUNSCREEN AGENTS

BACKGROUND OF THE INVENTION

The higher esters of substituted cinnamic acids, particularly the octyl methoxy cinnamates, are well known sunscreen agents which possess high absorption in the 300–400 nm range and which are ideally suited for cosmetic applications since they are non-irritating to the skin and provide lubricity to prevent drying effects of wind and sun. However, a major consideration in the use of such cinnamates is economic. The high production costs associated with substantial product losses during the current stripping and washing stages coupled with the generation of highly acidic wastes which must be neutralized before disposal in order to satisfy environmental regulations, is mainly responsible for the cost of the cinnamate products. Other important factors contributing to product cost are a relatively low product yield, the formation of undesirable phenyl ester, dimer and polymer cinnamate by-products during the slow rate of transesterification in current processes and the use of environmentally objectionable aromatic solvents and their decomposition products which require dilution before release to the atmosphere.

Accordingly, it is an object of this invention to provide a process for the manufacture of alkoxy cinnamate esters which eliminates or minimizes the volume of material requiring neutralization or dilution of harmful effluents generated in the system.

Another object of the invention is to provide a commercially feasible process which reduces the cost of alkoxy cinnamate manufacture by at least 10 per cent.

Still another object of the invention is to provide an integrated, continuous process for the production of alkoxy cinnamate sunscreen agents.

Yet another object is to provide a process for the conversion of lower alkoxybenzaldehyde to a higher alkyl alkoxy cinnamate which significantly eliminates or minimizes acidic waste and venting of toxic vapors.

Another object is to provide a self-sustaining process, ideally suited for continuous operation, which greatly reduces the volume of waste and treatment thereof.

These and other objects of the invention will become apparent from the following description and disclosure.

THE INVENTION

In accordance with the present invention there is provided a process for the economical production of a $C_5$ to $C_{14}$ alkyl $C_1$ to $C_4$ alkoxycinnamate in significantly improved yield and purity which comprises:

(a) dissolving a water insoluble $C_1$ to $C_4$ alkoxybenzaldehyde and a $C_1$ to $_4$ alkyl acetate in a common hydrocarbon solvent;

(b) reacting the resulting solution in the presence of a strong alkali metal base under mild conditions to form a mixture containing the corresponding $C_1$ to $C_4$ alkyl $C_1$ to $C_4$ alkoxycinnamate, the alkali metal salt of the enol corresponding to said $C_1$ to $C_4$ alkyl $C_1$ to $C_4$ alkoxycinnamate, the alkali metal salt of $C_1$ to $C_4$ alkoxycinnamic acid and a $C_1$ to $C_4$ alkanol;

(c) acidifying the resulting mixture with from about 0.4 to about 1 mole of a strong polybasic acid per mole of base to generate acetic acid, to convert the alkali metal salt of the $C_1$ to $C_4$ alkoxy cinnamic acid to the corresponding acid and to form an alcohol suspension of said alkali metal salts of said strong polybasic acid so as to maintain a mole ratio of monovalent to divalent acid ions in the suspension of between about 1:10 and about 20:1;

(d) esterifying said acetic acid by reacting with a $C_1$ to $C_4$ alkanol and stripping the esterified acetic acid from the mixture;

(e) reacting the remaining $C_1$ to $C_4$ alkyl $C_1$ to $C_4$ alkoxycinnamate and $C_1$ to $C_4$ alkoxycinnamic acid with a $C_5$ to $C_{14}$ alkanol in the presence of said alkali metal salt of said strong polybasic acid suspension at a temperature of from about 60° to about 130° C. and (f) recovering $C_5$ to $C_4$ alkyl $C_1$ to $C_4$ alkoxycinnamate as the product of the process.

The present process can be operated in batch, semi-batch or continuous mode. In the preferred semi-batch or continuous modes of operation, the process can be self-regenerating, nearly approaching total recycle of effluents generated and separated in various stages of the process, as is explained hereinafter.

The common solvents employed in solubilizing step (a) include aliphatic or alicyclic solvents such as octane, heptane, cyclohexane, a narrow petroleum cut boiling between about 100° and about 150° C., etc. and aromatic solvents such as for example, toluene, xylene, etc.; however, the aliphatic, alicyclic or mixtures of these solvents are preferred for ecological reasons. In general, the reactants in stage (a) are present in between about 10 wt. % and about 80 wt. % concentration and the mole ratio of aldehyde to acetate is between about 1:1.5 and about 1:5.

The alkali metal base, which performs a catalytic function in condensation reaction (b) is suitably an inorganic compound, e.g. metallic sodium, sodium hydride, etc. or an organic compound, such as a sodium or potassium amide, a sodium, potassium or lithium $C_1$ to $C_4$ alkoxide, particularly potassium tert-butoxide, sodium methoxide, sodium ethoxide, potassium ethoxide and the like; sodium $C_1$–$C_2$ alkoxides being preferred. The concentration of base can vary between about 2 wt. % and about 30 wt. % of the reaction mixture or from about 100 mol % to about 300 mol % of reactant aidehyde. The reactants are preferably employed in a double or triple stoichiometric excess of the alkyl acetate.

The condensation reaction is effected under mild conditions which include a temperature of between about 20° and about 90° C. for a period of from about 1 to about 10 hours; more desirably at 40°–65° C. for 2–6 hours. During this stage, the aldehyde or a mixture of $C_1$ to $C_4$ alkoxyaldehydes is reacted with the alkyl acetate or a mixture of $C_1$ to $C_4$ alkyl acetates to provide a mixture containing the corresponding $C_1$ to $C_4$ alkyl $C_1$ to $C_4$ alkoxy cinnamate, the alkali metal salt of the enol corresponding to the $C_1$ to $C_4$ alkyl $C_1$ to $C_4$ alkoxy cinnamate, the alkali metal salt of $C_1$ to $C_4$ alkoxy cinnamic acid and the $C_1$ to $C_4$ alkanol. This condensation reaction mixture is subjected to acidification with between about 0.5 to about 1 mole of a strong polybasic acid per mole of base. The strong polybasic acids suitable for acidification in step (c) include inorganic acids such as sulfuric acid and phosphoric acid as well as organic polybasic acids such as oxalic acid, succinic acid and benzene disulfonic acid. The addition of the polybasic acid, among its other functions, serves to neutralize any excess base at this stage of the process and to cleave alkali metal salts of acidic components formed in step (a), thereby releasing acetic acid. Additionally, the acid salts of the polybasic acid promote esterification of the liberated acetic acid with a lower alkanol, preferably a $C_1$ to $C_4$ alkanol generated in the condensation reaction as a by-product. The resulting $C_1$ to $C_4$ alkyl acetate is then stripped or otherwise removed along with $C_1$ to $C_4$ alkanol and hydrocarbon solvent, which components can be subsequently separated and recycled to the appropriate stages of the process. The separation of the acetate, alkanol and hydrocarbon solvent from the $C_1$ to $C_4$ alkyl $C_1$ to $C_4$ alkoxy cinnamate and $C_1$ to $C_4$ alkoxycinnamic acid components is carried out at a temperature of between about 50° and about 120° C., more desirably between about 60° and about 100° C. over a period of from 0.5 to 10 hours, e.g. 1–4 hours.

The acidification represents a critical step in the process, since it is this stage which controls the formation of effluents suitable for recycle in the overall process through the generation in situ of the catalyst needed for esterification of the acetic acid as well as for the subsequent transesterification of $C_1$ to $C_4$ alkyl $C_1$ to $C_4$ alkoxycinnamate and $C_1$ to $C_4$ alkoxycinnamic acid to the desired $C_5$ to $C_{14}$ alkyl $C_1$ to $C_4$ alkoxycinnamate product of the process. The high efficiency of the catalyst in the present invention relates to the specifics of the interaction of the strong acids with the bases in a non-aqueous system. This interaction leads to the formation of suspended particles of complex structure incorporating both neutral salt, eg. $Na_2SO_4$, and acidic salt, e.g. $NaHSO_4$. Each particle acts as a buffered acid catalyst system, where the acidity of eg. $HSO_4^-$ is moderated. Control of the neutral/acidic salt ratio allows for the optimization of both acidity and particle size in the suspension. It is recognized that sulfuric acid is a stronger acid than benzene disulfonic acid and that the latter is stronger than oxalic acid; thus, the efficient ratio of (alkali metal)(H)(acyl residue)/(Alkali metal)2(acyl residue) can vary from about 1:10 to about 20:1 (molar), preferably from about 1:4 to about 10:1 (molar).

In the present process, after the removal of acetate, alkanol and solvent in step (c), the remaining $C_1$ to $C_4$ alkyl $C_1$ to $C_4$ alkoxycinnamate and $C_1$ to $C_4$ alkoxycinnamic acid are reacted with a $C_5$ to $C_{14}$ alkanol at a temperature of from about 60° to about 130° C. over a period of from about 0.5 to about 10 hours, preferably from about 90° to about 110° C. for about 2 to about 4 hours. This transesterification reaction is carried out with stoichiometric amounts of reactants or with up to a four fold molar excess of alcohol in the presence of the catalyst alcohol and solvent suspension generated in step (c) of the process. If desired, the catalyst suspension can be augmented with a small amount, e.g. up to 5 wt % of the same or other acidic catalyst, such as methane sulfonic acid or p-toluene sulfonic acid.

Upon completion of the transesterification reaction, the $C_5$ to $C_{14}$ alkyl $C_1$ to $C_4$ alkoxycinnamate is recovered in a high yield and selectivity, for example, yields in excess of 85% and selectivities greater than 90% can be achieved, as compared with 70% yields currently obtained in prior processes.

The recovery of product can be effected by stripping or distillation, preferably by fractional distillation, so as to separately collect fractions of the hydrocarbon solvent and the $C_1$ to $C_4$ alkanol, thus enabling recycle to the appropriate stages of (a) and (b) in the process. When carried out in a continuous manner, the later method of product recovery allows for more than 90% recycle of by-product effluents, which greatly reduces the volume of waste previously obtained requiring processing before disposal. Additionally, any small amount of waste from the present process is obtained in a less concentrated acid state, thus requiring little, if any, neutralization before disposal. The source of waste product mixture from step (d) to strip recycle and waste components prior to distillation. The washing of product can be carried out in 1 to 4 stages and sodium bicarbonate can be added to a second or a subsequent wash to remove traces of acidity from the wash water; thus, direct disposal of waste materials poses no problem.

Having broadly described the present process, reference is now had to the following examples which illustrate preferred embodiments but which are not to be construed as limiting to the scope of the invention as set forth in the foregoing discussion and in the appended claims.

EXAMPLE 1

Into a 1,000 ml glass reactor was introduced 90 g. (0.66 mole) of p-methoxy benzaldehyde and 110 g. (1.44 mole) of methyl acetate dissolved in 180 ml (135 g.) of a petroleum fraction boiling at about 115°–120° C. and 38 g. (0.70 mole) of sodium methoxide was added to catalyze the condensation reaction which took place at a temperature of 50° C. over a period of 4 hours.

The resulting condensation product mixture was then acidified by introducing 52 g. (0.53 mole) of $H_2SO_4$ and 46 g. of methanol under agitation, whereupon acetic acid was liberated and cleavage of sodium acetate resulted in the formation of an alcoholic/hydrocarbon suspension of $NaHSO_4/Na_2SO_4$ with a mole ratio of sodium hydrogen sulfate to sodium sulfate of about 1:1.

The temperature of the resulting acidified mixture was slowly raised to about 100° C. and the methyl acetate, methanol, reaction water and about 20% of the solvent were removed from the methyl methoxycinnamate and methoxycinnamic acid solution containing the remaining 80% of solvent. The components removed were separated and 59.2 g. (0.8 mole) of methyl acetate was recycled as reactant for the condensation along with 27 g. of solvent while 40 g. of methanol was recycled to the acidification stage for the generation of sodium bisulfate/sodium sulfate catalyst suspension. Then 172 g. (1.32 mole) of 2-ethylhexanol were added to the suspension, and the resulting mix was held at 105°–110° C. for 8 hours while stripping the transesterification and esterification by-products (methanol and water) and most of the remaining hydrocarbon solvent. After distillate layer separation 90 g. of the solvent was recycled to the synthesis stage; 23 g. of aqueous methanol were discarded into waste. This stream could be used in the methanol recovery/recycling process.

Resulting suspension of the sodium sulfate and hydrogen sulfate in 2-ethylhexylmethoxycinnamate, containing also reaction by-products and the remaining hydrocarbon solvent was consequently washed with 150 ml of hot water, 150 ml of 1% sodium bicarbonate solution, and then 150 ml of hot water. Amber-colored organic layer was stripped of the remaining hydrocarbon solvent (15 g. of the solvent was recycled to the synthesis stage). Then it was vacuum distilled at the residual pressure of 20-2 mm Hg to obtain 84 g. of 2-ethylhexanol recycled to the transesterification stage, 23 g. of the intermediate fraction, 162 g. of 2-ethylhexyl methoxycinnamate (85 mol. % of theoretical yield), and 21 g. of the heel.

EXAMPLE 2

Example 1 was repeated except that during the acidification step, 61 g. of sulfuric acid (0.62 mole) were added to provide a mole ratio of sodium hydrogen sulfate to sodium sulfate of 3:1. Transesterification time at 105°–110° C. was 2 hours, and the amounts of the intermediate fraction, 2-ethylhexyl methoxycinnamate and the heel recovered by the distillation were 22 g., 167 g. (87 mol. % of theoretical yield), and 17 g.

EXAMPLE 3

Total Recycle of Methyl Acetate

Example 2 was repeated except that during the acidification step, the amount of methanol added was increased to 70 g., and additionally 42 g. (0.7 mole) of acetic acid was added. Methyl acetate (110 g.) was recovered for recycling to the condensation stage, and methanol (70 g.) was recovered for recycling to the acidification stage.

Distillation of the final product yielded 166 g. (87 mol. %) of 2-ethylhexyl methoxycinnamate.

EXAMPLE 4

Use of High $NaHSO_4/Na_2SO_4$ Ratio

Example 1 was repeated, except that during the acidification stage, 67 g. of sulfuric acid (0.68 mole) were added to provide a mole ratio of sodium hydrogen sulfate to sodium sulfate of 25:1. Transesterification time at 105°–110° C. was 0.5 hours, and the amounts of the intermediate fraction, 2-ethylhexyl methoxycinnamate and the heel recovered by the distillation were 17 g., 159 g. (83 mol. % of theoretical yield), and 29 g.

EXAMPLE 5

Use of Heptane Solvent

Example 2 was repeated except that during the condensation step 190 ml (130 g.) of n-heptane is used instead of the hydrocarbon solvent boiling at 115°–120° C. Total amount of heptane recovered in further process stages for the reuse was 116 g.

Distillation of the final product yielded 164 g. (85.5 mol. %) of 2-ethylhexyl methoxycinnamate.

EXAMPLE 6

Use of Oxalic Acid

Example 4 was repeated, except that during the acidification stage 61 g. of oxalic acid (0.68 mole) were added to provide a mole ratio of sodium hydrogen oxalate to sodium oxalate of 125:1. The transesterification time at 115°–120° C. was 8 hours, and the amounts of the intermediate fraction, 2-ethylhexyl methoxycinnamate and the heel recovered by the distillation were 30 g., 161 g. (84 mol. % of theoretical yield), and 14 g.

What is claimed is:

1. The process of producing a $C_5$ to $C_{14}$ alkyl $C_1$ to $C_4$ alkoxycinnamate in significantly improved yield and purity which comprises:

(a) dissolving a water insoluble $C_1$ to $C_4$ alkoxybenzaldehyde and a $C_1$ to 4 alkyl acetate in a common hydrocarbon solvent;

(b) reacting the resulting solution in the presence of a strong alkali metal base under mild conditions to form a mixture containing the corresponding $C_1$ to $C_4$ alkyl $C_1$ to $C_4$ alkoxycinnamate, the alkali metal salt of the enol corresponding to said $C_1$ to $C_4$ alkyl $C_1$ to $C_4$ alkoxycinnamate, the alkali metal salt of $C_1$ to $C_4$ alkoxy cinnamic acid and a $C_1$ to $C_4$ alkanol;

(c) acidifying the resulting mixture with from about 0.4 to about 1 mole of a strong polybasic acid per mole of base to generate acetic acid, to convert the alkali metal salt of $C_1$ to $C_4$ alkoxycinnamic acid to the corresponding acid and to form a solvent suspension of said alkali metal salt of said strong polybasic acid so as to maintain a mole ratio of monovalent to divalent acid ions in the suspension of between about 1:10 and about 20:1;

(d) esterifying said acetic acid by reacting with a $C_1$ to $C_4$ alkanol and stripping the esterified acetic acid from the mixture;

(e) reacting the remaining $C_1$ to $C_4$ alkyl $C_1$ to $C_4$ alkoxycinnamate and $C_1$ to $C_4$ alkoxycinnamic acid with a $C_5$ to $C_{14}$ alkanol in the presence of said alkali metal salt of said strong polybasic acid suspension at a temperature of from about 60° to about 130° C. and (f) recovering $C_5$ to $C_{14}$ alkyl $C_1$ to $C_4$ alkoxycinnamate as the product of the process.

2. The process of claim 1 wherein said common hydrocarbon solvent is heptane.

3. The process of claim 1 wherein said common solvent is a petroleum fraction boiling between about 100° and about 150° C.

4. The process of claim 1 wherein said base is an alkali metal $C_1$ to $C_4$ alkoxide.

5. The process of claim 1 wherein a mixture of $C_1$ to $C_4$ alkyl $C_1$ to $C_4$ alkoxybenzaldehydes are employed.

6. The process of claim 1 wherein a mixture of $C_1$ to $C_4$ alkyl acetates are employed.

7. The process of claim 1 wherein sulfuric acid is the strong polybasic acid.

8. The process of claim 7 wherein an alkali metal hydrogen sulfate/alkali metal sulfate in a mole ratio of from about 1:10 to about 20:1 is suspended in a mixture of the alcohol generated in step (b) of the process and the common hydrocarbon solvent.

9. The process of claim 6 wherein the alkanol of step (d) is a mixture of $C_1$ to $C_4$ alkanols derived from the use of a corresponding mixture of $C_1$ to $C_4$ alkyl acetates employed in step (a).

10. The process of claim 1 wherein the esterified acetic acid, $C_1$ to $C_4$ alkanol and said solvent are stripped from cinnamate and cinnamic components in step (d).

11. The process of claim 10 wherein said stripped esterified acetic acid together with said solvent is separated from said $C_1$ to $C_4$ alkanol and recycled to step (a) of the process.

12. The process of claim 11 wherein said $C_1$ to $C_4$ alkanol is recycled to step (c) of the process.

13. The process of claim 1 wherein p-methoxy benzaldehyde is reacted with methyl acetate in step (a); methyl p-methoxycinnamate is formed in step (b) and methyl p-methoxycinnamate and p-methoxycinnamic acid are reacted with a $C_8$ alkanol in step (e) to produce a $C_8$ alkyl p-methoxycinnamate as the product of the process.

14. The process of claim 1 wherein p-methoxy benzaldehyde is reacted with ethyl acetate in step (a); ethyl p-methoxycinnamate is formed in step (b) and ethyl p-methoxycinnamate and p-methoxycinnamic acid are reacted with a $C_8$ alkanol in step (e) to produce a $C_8$ alkyl p-methoxycinnamate as the product of the process.

15. The process of claim 13 or 14 wherein said $C_8$ alkanol is 2-ethylhexanol and the product of the process is 2-ethylhexyl p-methoxycinnamate.

16. The process of claim 1 wherein step (a) of the process is effected at a temperature between about 40° and about 65° C.; stripping in step (c) is carried out at a temperature of between about 60° and about 100° C. and step (d) is carried out at a temperature of between about 90° and about 110° C.

17. The process of claim 1 wherein the product in step (f) is recovered by fractional distillation.

18. The process of claim 17 wherein the hydrocarbon solvent and a $C_5$ to $C_{14}$ alkanol by-product are separately recovered from said distillation, the hydrocarbon solvent is recycled to step (a) and the $C_5$ to $C_{14}$ alkanol is recycled to step (e) of the process.

19. The process of claim 1 wherein upon completion of esterification in step (e), the product mixture is water washed in from 1 to 4 stages to remove the catalytic salts of the polybasic acid.

20. The process of claim 19 wherein a plurality of water washing stages are employed and a neutralizing amount of sodium bicarbonate is added to the second water wash.

* * * * *